US008377979B2

(12) United States Patent
Blumberg et al.

(10) Patent No.: US 8,377,979 B2
(45) Date of Patent: Feb. 19, 2013

(54) PHARMACEUTICAL FORMULATION CONTAINING PHENYTOIN SODIUM AND MAGNESIUM STEARATE

(75) Inventors: Tamar Blumberg, Kfar Sava (IL); Orit Brodzsky, Kiryat Haim (IL); Nataly Zissman, Nesher (IL); Avraham Yacobi, Englewood, NJ (US)

(73) Assignee: Taro Pharmaceuticals North America, Inc., Grand Cayman (KY)

( * ) Notice: Subject to any disclaimer, the term of this patent is extended or adjusted under 35 U.S.C. 154(b) by 63 days.

(21) Appl. No.: 11/633,507

(22) Filed: Dec. 5, 2006

(65) Prior Publication Data

US 2007/0185180 A1 Aug. 9, 2007

Related U.S. Application Data

(60) Provisional application No. 60/742,319, filed on Dec. 5, 2005.

(51) Int. Cl.
*A61K 9/48* (2006.01)
*A61K 9/52* (2006.01)

(52) U.S. Cl. .......................... 514/389; 424/452; 424/457

(58) Field of Classification Search .................. 514/389; 424/452, 457
See application file for complete search history.

(56) References Cited

U.S. PATENT DOCUMENTS

| | | | |
|---|---|---|---|
| 2,409,754 A | 10/1946 | Henze | |
| 3,598,122 A | 8/1971 | Zaffaroni | |
| 3,598,123 A | 8/1971 | Zaffaroni | |
| 3,728,445 A * | 4/1973 | Bardani | 424/465 |
| 4,642,316 A | 2/1987 | Fawzi et al. | |
| 4,696,814 A | 9/1987 | Kao et al. | |
| 5,863,558 A | 1/1999 | Jao et al. | |
| 5,955,103 A | 9/1999 | Jao et al. | |
| 5,968,554 A | 10/1999 | Beiman et al. | |
| 6,274,168 B1 | 8/2001 | Addicks et al. | |
| 6,620,432 B2 | 9/2003 | Addicks et al. | |
| 2001/0043945 A1 | 11/2001 | Addicks et al. | |
| 2006/0034910 A1 | 2/2006 | Patel et al. | |
| 2006/0222713 A1 | 10/2006 | Murpani et al. | |

FOREIGN PATENT DOCUMENTS

WO WO 2007/067508 6/2007

OTHER PUBLICATIONS

Gugler et al. "The Bioavailability of Phenytoin". Journal of Neurology. 1977. vol. 216. pp. 155-162.*
Bronlund et al. (International Dairy Journal (2004); 14:247-254).*
*Journal of Neurological Sciences*, 16: 481-487, 1972.
*Pharmaceutical Sciences*, Remington, 18th Ed., Mack Publishing Co. 1990, p. 1078.
Goodman & Gilman's, *The Pharmacological Basis of Therapeutics*, J. Harman et al. eds., p. 468-469, 9th Edition, McGraw-Hill, New York, 1996.
*Pharmaceutical Sciences*, Remington, 18th Ed., 1990, Mack Publishing Co. pp. 1676-1686.
*The Pharmaceutical and Clinical Pharmacokinetics*, 3rd Ed., 1984, Lea and Febiger, Philadelphia, pp. 1-28.
Handbook of Pharmaceutical Excipients, 5th Edition, Rowe et al. eds., pp. 430-433, Pharmaceutical Press, 2006.
Remington, *The Science and Practice of Pharmacy*, Gennaro A. ed., p. 681-699, 20th Edition, Lippincott, 2000.
Gibaldi et al., Pharmacokinetics. 2.sup.nd Ed. Marcel Dekker, Inc., 1982—Table of Contents.
Yeh et al., A comparison of numerical integrating algorithms by trapezoidal, lagrange, and spline approximations. J. Pharmacokinet Biopharm. 6:79 (1978).
International Search Report, mailed Oct. 2, 2007, PCT/US06/46323.
International Preliminary Report on Patentability, mailed Jun. 19, 2008, PCT/US06/46323.

* cited by examiner

*Primary Examiner* — James D Anderson
*Assistant Examiner* — Chris Simmons
(74) *Attorney, Agent, or Firm* — Venable LLP; Michael A. Gollin; Thomas F. Barry

(57) ABSTRACT

The present invention relates to a novel pharmaceutical formulation comprising phenytoin sodium, a high amount of magnesium stearate, and a low level of a hydrophilic polymer such as a methocel, and a method of preparing the same by blending.

14 Claims, 1 Drawing Sheet

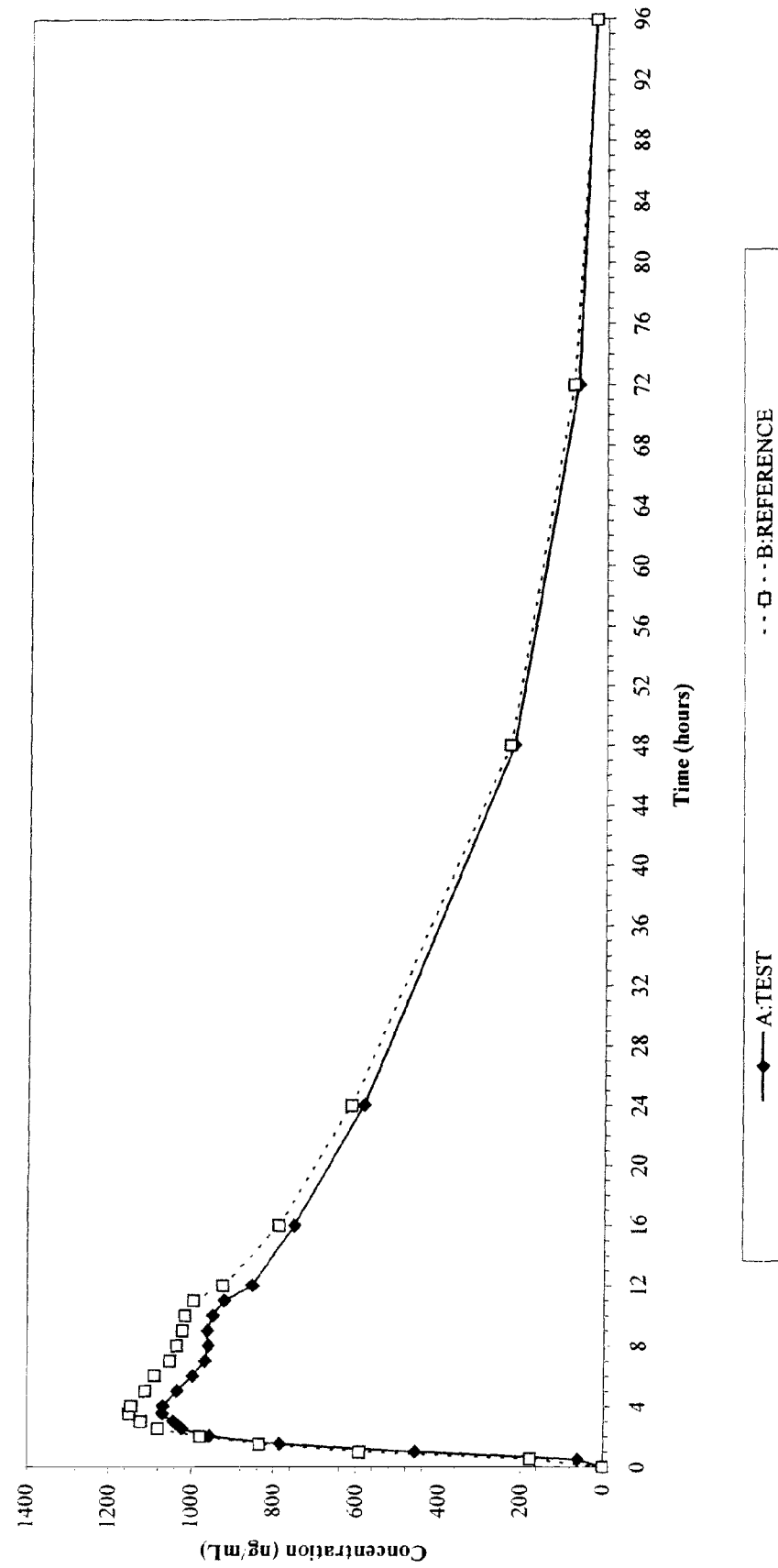

PHARMACEUTICAL FORMULATION CONTAINING PHENYTOIN SODIUM AND MAGNESIUM STEARATE

FIELD OF THE INVENTION

The present invention pertains to a formulation containing phenytoin sodium which exhibits an extended release profile. In particular, the present invention concerns a pharmaceutical composition comprising phenytoin sodium and magnesium stearate.

BACKGROUND

Epilepsy is a central nervous system disorder characterized by the repeated occurrence of sudden and transitory episodes of abnormal phenomena of motor, convulsion, sensory, autonomic, or psychic origin. The disorder afflicts millions of people worldwide, and occurs more commonly in children than in adults.

Phenytoin (5,5-diphenyl-2,4-imidazolidinedione) and its alkali metal salts (e.g., sodium, lithium and potassium) represent antiepileptic drugs. The indication for phentyoin includes control of generalized tonic-clonic (grand mal) seizures and complex partial seizures (temporal lobe psychomotor). See, *Pharmaceutical Sciences*, Remington, 18th Ed., Mack Publishing Co. 1990, pp. 1078. The primary site of action for phenytoin appears to be the cerebral motor cortex where spread of seizure activity is inhibited.

Upon ingestion and exposure in the gastrointestinal pH range of 1 to 8, phenytoin sodium is converted to phenytoin which is practically insoluble because it is a relatively weak acid (pKa=8.3). Phenytoin's insolubility makes it difficult to deliver a dosage form of phenytoin which has a consistent dissolution profile over an extended period of time. The plasma half-life in man after oral administration of phenytoin averages 22 hours, with a range of 7 to 42 hours. Steady-state therapeutic levels are achieved at least 7 to 10 days (5-7 half-lives) after initiation of therapy with recommended doses of 300 mg/day. Because clinically significant toxicity can be encountered after administration of phenytoin, proper dosing is essential. Goodman & Gilman's, *The Pharmacological Basis of Therapeutics*, J. Harman et al. eds., pg. 468-469, 9$^{th}$ Edition, McGraw-Hill, New York, 1996. In order to control seizures while avoiding the side effects of the medication, phenytoin dosing requires optimization. Serum level determination is necessary for optimal dosage adjustments to maintain concentrations of phenytoin in the therapeutic range of 10 and 20 µg/mL. In general, the initial adult dosage of phenytoin is 100 mg three times daily. For most adults, a satisfactory maintenance dose will be 300 mg or 400 mg a day. Peak levels indicate an individual's threshold for dose-related side effects and are obtained at the time of expected peak concentration. Conventional dosage forms and their mode of operation, including dose peaks and valleys, are discussed in details in *Pharmaceutical Sciences*, Remington, 18th Ed., 1990, Mack Publishing Co. pp. 1676-1686; *The Pharmaceutical and Clinical Pharmacokinetics*, 3rd Ed., 1984, Lea and Febiger, Philadelphia, pp. 1-28; and in U.S. Pat. Nos. 3,598,122 and 3,598,123.

Phenytoin sodium is currently available in the U.S. in a number of different dosage forms. For example, dosage forms include an immediate release or "prompt" capsule, an extended release capsule, a chewable tablet, an oral suspension, and a parenteral solution. The "prompt" phenytoin sodium capsules exhibit a rapid rate of absorption with peak blood concentration in 1.5 to 3 hours. Because rapid release can lead to the development of undesirable toxic effects, the use of "prompt" phenytoin sodium is not recommended.

Several dosage systems have since been developed and marketed to provide an extended release dosage form and for reducing the number of daily administrations. For example, extended release formulations containing 30 and 100 mg phenytoin sodium are marketed by Warner-Lambert/Parke-Davis under the brand name Dilantin®. Dilantin® capsules contain 30 or 100 mg phenytoin sodium, lactose, confectioner's sugar, talc, and magnesium stearate as a loose powder and band sealed. In contrast to the "prompt" form of phenytoin sodium, the Dilantin® formulation exhibits a slower dissolution with prolonged absorption of the drug substance.

Other extended release formulations containing 200 and 300 mg phenytoin sodium are commercially available under the brand name Phenytek®. These extended release capsules contain 200 or 300 mg phenytoin sodium in an erodible matrix that includes povidone, hydroxyethyl cellulose, microcrystalline cellulose, magnesium oxide, colloidal silicon dioxide and magnesium stearate as disclosed in U.S. Pat. Nos. 6,274,168 and 6,620,432. The extended release capsules provide a peak serum level at 4 to 12 hours after administration.

Additional dosage forms exist and they involve enteric coating modifications in order to control the drug release. For example, U.S. Pat. No. 5,968,554 discloses a sustained release formulation containing phenytoin, a first enteric coating over the core, a second coating of the active ingredient, and a third coating that is soluble in gastric juices. U.S. Pat. No. 5,863,558 discloses a sustained release formulation containing a nonionic polymer that prevents the contact of phenytoin sodium with the gastrointestinal environment. This dosage form includes at least one exit in the inert wall surrounding the internal compartment and the wall maintains its integrity during the drug release.

U.S. patent application Ser. No. 11/199,169 discloses an extended release formulation containing phenytoin sodium and hydroxypropyl methyl cellulose; however, the manufacturing process in the application involves the use of methylene chloride and isopropyl alcohol. Methylene chloride is considered a Class 2 solvent by the United States Food and Drug Administration and its presence in any pharmaceutical product is strictly limited (www.fda.gov, Guidance for Industry, Q3C—Tables and List).

Other modes of antiepileptic drug administration include a nonrate-controlling, dose-dumping capsule, or a nonrate-controlling, dose-dumping tablet, and usually at multiple, repetitive dosing intervals. This prior-art mode of therapy leads to an initial high dose of drug in the blood, followed by a decreased dose of drug in the blood.

There is a continuing need for the development of pharmaceutical formulations of phenytoin sodium that provide for a controlled rate of release over an extended period of time.

SUMMARY OF THE INVENTION

The present invention provides for a pharmaceutical formulation of phenytoin sodium comprising, from about 10% (w/w) to about 90% (w/w) phenytoin sodium, from about 6% (w/w) to about 20% (w/w) magnesium stearate and from about 1% (w/w) to about 7% (w/w) of a hydrophilic polymer. The hydrophilic polymer may be hydroxypropylmethyl cellulose, hydroxypropyl starch, hydroxypropyl cellulose, hydroxyethyl cellulose, carboxymethyl cellulose, polyethylene oxide, acacia, guar gum, tragacanth gum, xanthan and mixtures thereof. In a preferred embodiment, the hydrophilic polymer is hydroxypropylmethyl cellulose.

In one embodiment, the pharmaceutical formulation comprises from about 40% (w/w) to about 45% (w/w) phenytoin sodium, from about 6% (w/w) to about 10% (w/w) magnesium stearate, and from about 1% (w/w) to about 5% (w/w) hydroxypropylmethyl cellulose; in a preferred embodiment, the pharmaceutical formulations has about 40% phenytoin sodium, about 9% (w/w) magnesium stearate and about 4% hydroxypropylmethyl cellulose.

Additionally, the pharmaceutical formulation may have about 5% (w/w) to about 15% (w/w) talc and about 15% (w/w) to about 25% (w/w/) lactose monohydrate.

The in vitro dissolution profile for phenytoin sodium when testing using USP apparatus I in water at 75 rpm may be: (i) from about 20% (w/w) to about 40% (w/w) released in 30 minutes; (ii) from about 40% (w/w) to about 85% (w/w) released in 60 minutes; and, (iii) not less than 70 percent (w/w) released in 120 minutes. A peak plasma level of phenytoin may be obtained from about 4.5 hours to about 11 hours after oral administration.

Additionally, the pharmaceutical formulation may comprise binders, glidants, lubricants, diluents, disintegrants and mixtures thereof.

The invention also describes a process for preparing a pharmaceutical phenytoin sodium formulation comprising, the steps of: (a) screening a mixture of phenytoin sodium and a hydrophilic polymer through a 30 mesh sieve; (b) screening magnesium stearate through a 60 mesh; and, (c) blending the phenytoin sodium, hydrophilic polymer from step (a) and magnesium stearate from step (b) together. The blend may be a dry blended powder. The pharmaceutical formulation prepared by such process may comprise, from about 10% (w/w) to about 90% (w/w) phenytoin sodium, from about 6% (w/w) to about 20% (w/w) magnesium stearate and from about 1% (w/w) to about 7% (w/w) of a hydrophilic polymer, where the hydrophilic polymer is selected from the group consisting of hydroxypropylmethyl cellulose, hydroxypropyl starch, hydroxypropyl cellulose, hydroxyethyl cellulose, carboxymethyl cellulose, polyethylene oxide, acacia, guar gum, tragacanth gum, xanthan and mixtures thereof. In a preferred embodiment, the pharmaceutical formulation comprises, from about 40% (w/w) to about 45% (w/w) phenytoin sodium, from about 6% (w/w) to about 10% (w/w) magnesium stearate, and from about 1% (w/w) to about 5% (w/w) hydroxypropylmethyl cellulose. The pharmaceutical formulation prepared by the process of the invention may comprise from about 5% (w/w) to about 15% (w/w) talc and from about 15% (w/w) to about 25% (w/w/) lactose monohydrate.

BRIEF DESCRIPTION OF THE DRAWING

FIG. 1 shows the mean plasma concentration over time of the pharmaceutical formulation of the present invention as compared with the reference standard product.

DETAILED DESCRIPTION

Definitions:

Unless defined otherwise, all technical and scientific terms used herein have the meaning as commonly understood by one of ordinary skill in the art to which this invention belongs.

In the specification, the following terms are defined: "PK" refers to an abbreviation of pharmacokinetic; "Ln" refers to natural log; "AUC" refers to the mean area under the plasma concentration-time curve; "$AUC_{0-t}$" refers to area under the concentration-time curve from time zero to the time of the last sample collection; "$AUC_{0-\infty}$" refers to area under the concentration-time curve from time zero to infinite hours; "$C_{max}$" refers to maximum observed plasma concentration; "$T_{max}$" (or "$t_{max}$") refers to the time to achieve the $C_{max}$; and, "$t_{1/2}$" refers to the apparent half-life and is calculated as (ln $2/K_e$), where $K_e$ refers to the elimination rate constant.

In accordance with the present invention, pharmacokinetic parameters were calculated using standard non-compartmental methods, as implemented in software designed for pharmacokinetic, pharmacodynamic, and noncompartmental analysis, marketed by Pharsight Corporation under the trademark WinNonlin™. Version 4.0.1 of this software was used. The mean, standard deviation (SD) and percent coefficient of variations (CV (%)) were calculated for plasma concentrations of phenytoin for each sampling time and for each treatment.

Areas under the concentration-time curves (AUC) were determined with respect for each human subject that received oral administration of an extended-release formulation of phenytoin salt. $AUC_{0-t}$ was calculated using the linear trapezoidal rule, which employs an approximate integration formula. The area of each trapezoid was calculated, and the sum of all the areas of all the trapezoids yielded an estimate of the true area under the curve. (See, Gibaldi et al. *Pharmacokinetics*. $2^{nd}$ Ed. Marcel Dekker, Inc., 1982; Yeh et al., A comparison of numerical integrating algorithms by trapezoidal, lagrange, and spline approximations. *J. Pharmacokinet Biopharm.* 6:79 (1978). $C_{max}$ and $T_{max}$ were then determined for each concentration vs. time profile. Elimination rate constant ($K_e$) was calculated using regression analyses on the natural log (ln) of plasma concentration values (y) versus time (x).

The composition of the present invention comprises phenytoin sodium and magnesium stearate in an amount sufficiently high enough to control the release of phenytoin sodium over an extended period of time, i.e., provide for a controlled or extended-release formulation.

Magnesium stearate is hydrophobic. When incorporated into a formulation containing an active pharmaceutical ingredient ("API"), magnesium stearate may retard the dissolution of an API from a solid dosage form; however, the rate of dissolution appears to be very sensitive to the amount of magnesium stearate incorporated into the formulation. Handbook of Pharmaceutical Excipients, $5^{th}$ Edition, Rowe et al. eds., pp. 430-433, Pharmaceutical Press, 2006. In addition, the rate of dissolution appears to depend on the presence of other ingredients in the pharmaceutical formulation. Because phenytoin can exhibit numerous side effects if the plasma blood levels are too high, it is critical to develop a formulation that will provide for proper dosing of the drug over an extended period of time, for example for 96 hours, and will overcome the problem of a comparatively high variability in the dissolution rate of the phenytoin.

The inventors of the present invention have surprisingly discovered that a comparatively high level of magnesium stearate, when mixed with phenytoin sodium, will retard the release of phenytoin sodium from the formulation to the same extent as the brand product, Dilantin®. Magnesium stearate may be mixed with phenytoin sodium in amounts ranging from about 6% (w/w) to about 20% (w/w). In a preferred embodiment, the amount of magnesium stearate incorporated into the formulation is from about 6% (w/w) to about 10% (w/w), more preferably about 9% (w/w). The formulations of the present invention comprise a homogeneous mixture of phenytoin salt and magnesium stearate. Using the formulations of the present invention, the blood levels of phenytoin sodium achieved after administration of these formulations match that obtained with Dilantin® over an extended period of time (0-96 hours).

The phenytoin used in the formulation of the present invention is preferably sodium; however, other phenytoin salts are encompassed by the invention, including, sodium, lithium, potassium, calcium and the like. Procedures for the manufacture of phenytoin sodium are well known (See, e.g., U.S. Pat. Nos. 4,696,814, 4,642,316, and 2,409,754). Additionally, any polymorphic form of phenytoin sodium may be used. In a preferred embodiment, the phenytoin sodium used in the pharmaceutical formulation of the present invention is a white powder with 95% of the particles having a particle size of less than 180 μm. In another embodiment, the phenytoin sodium is in the form of a bead, granule or pellet.

Phenytoin sodium may constitute up to about 90% of the dosage form. Preferably, the dosage form contains between about 25% to about 90% phenytoin sodium. More preferably, the dosage form contains between about 40% to about 60%. More preferably, the dosage form contains about 50%.

The dosage form may be a tablet, capsule or a powder for suspension. Preferably, the dosage form is formulated as a capsule. The preferred range of phenytoin salt in a capsule ranges from about 30 to 300 mg; more preferably, the phenytoin salt in a capsule is present in the amount of about 90 mg to 230 mg; still more preferably, the phenytoin salt is present in the amount of about 100 mg.

The pharmaceutical formulation may also incorporate at least one hydrophilic polymer. Examples of hydrophilic polymers, include, but are not limited to, methylcellulose, hydroxypropylmethyl cellulose, hydroxypropyl cellulose, carboxymethyl cellulose, ethyl cellulose, hydroxyethyl cellulose, polyethylene oxide, and the like. Preferably, the polymer is hydroxypropylmethyl cellulose. Preferably, the hydrophilic polymer is present in the amount from about 1% (w/w) to about 7% (w/w); more preferably, the hydrophilic polymer is present in the amount of about 4% (w/w). Various grades of hydroxypropylmethyl cellulose may be used, including, Methocel E15LV and Methocel K4M (Colorcon Inc, West Point, Pa., 19486).

Glidants or lubricants such as talc may be incorporated into the pharmaceutical formulation of the invention. Preferably, talc is present in the amount of about 5% (w/w) to about 15% (w/w). More preferably, talc is present in the amount of about 10% (w/w).

In addition to magnesium stearate and a hydrophilic polymer such as hydroxypropylmethyl cellulose, the pharmaceutical formulation of the present invention may contain a variety of additives or excipients. Examples of classes of additives include fillers, glidants, surface active agents, lubricants, buffering agents, disintegrating agents, stabilizers, water absorbing agents, pigments, flavoring agent, sweeteners, adjuvants and the like. The following represents a non-limiting list of these additives:

(i) fillers may include different grades of sugar, microcrystalline cellulose, polyalcohols, calcium hydrogen phosphate, calcium sulphate, pregelatinized starch;

(ii) glidants may include colloidal silicon oxide;

(iii) surface active agents may include sodium lauryl sulphate;

(iv) lubricants may include magnesium stearate, stearic acid, sodium stearyl fumarate;

(v) buffering agents may include sodium hydrogen phosphate sodium acetate;

(vi) disintegrating agents may include sodium starch glycolate, sodium stearyl fumarate, crospovidone;

(vii) water absorbing agents may include hydrophilic polymers as hydroxypropylmethyl cellulose, carbomer, sodium alginate;

(viii) pigments may include organic or inorganic pigments such as oxides of iron or titanium;

(ix) flavorants may include both natural and artificial flavors such as menthol, cinnamon; and, (x) sweeteners may include sucralose, saccharin sodium and confectioner's sugar.

These additives are to be used in amounts sufficient to achieve their intended purpose. Generally, the combination of these additives is used in amounts that do not modify the dissolution of the pharmaceutical formulation of the present invention.

Other additives that may be used, include excipients such as lactose monohydrate.

The pharmaceutical formulation of the present invention may be prepared by dry blending or dry mix technology, which consists of a thorough mixing of all ingredients to form a homogeneous mixture. Remington, *The Science and Practice of Pharmacy*, Gennaro A. ed., p. 681-699, 20$^{th}$ Edition, Lippincott, 2000. Dry mixing is feasible and may advantageously be used due to the components of the inventive formulations.

In one embodiment, lactose monohydrate, phenytoin sodium, talc, sugar and hydroxypropylmethyl cellulose are sieved through a 30 mesh screen. Magnesium stearate is sieved through a 60 mesh screen. The sieved materials are transferred to a V-blender and mixed. Mixing may require from about 10 minutes to about 60 minutes. In a preferred embodiment, mixing requires about 20 minutes. The blend is then filled into a gelatin capsule.

The pharmaceutical formulation of the present invention may include any solid dosage form suitable for oral administration. A dosage unit of the present formulation may consist of, for example, capsules, tablets, pills, pellets and the like. It is to be understood that the present invention is not to be construed as being limited to a particular dosage form. A preferred dosage form is a capsule.

Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety.

The embodiments illustrated and discussed in this specification are intended only to teach those skilled in the art the best way known to the inventors to make and use the invention. Nothing in this specification should be considered as limiting the scope of the present invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The following examples illustrate various aspects of the present invention. They are not to be construed to limit the claims in any manner.

EXAMPLES

Example 1

Commercial Phenytoin Sodium Extended-Release Capsules: Comparative Studies

Specific ingredients present in both Parke-Davis' and Mylan's extended-release phenytoin sodium caspules (i.e., Dilantin® and Mylan) were determined through reverse engineering. Table 1 summarizes some respective ingredients in the two commercial phenytoin sodium capsules.

TABLE 1

| Ingredients | Parke-Davis' Dilantin® 100 mg | Mylan's Extended Release Phenytoin 100 mg |
|---|---|---|
| Lactose[1] | 20.7% | Not tested |
| Magnesium Stearate[2] | 4.5% | 1.15% |
| Talc[3] | 2.3% | Not tested |

[1]Determined by HPLC
[2]Determined by both HPLC (stearic acid), and atomic absorption of magnesium.
[3]Determined by atomic absorption of Al, Mg and Si.

It is noteworthy that the level of magnesium stearate in the two commercial extended-release phenytoin sodium capsules does not exceed above 5%.

Example 2

Effect of Magnesium Stearate Level on Dissolution Rate

Magnesium stearate was blended with phenytoin sodium in a sequential mixing sequence as follows: (i) 3 hours mixing of phenytoin sodium and magnesium stearate; (ii) 30 minutes mixing with talc; and, (iii) 20 minutes mixing with lactose and compressible sugar. Capsules containing phenytoin sodium (formulation #1) were prepared having the following ingredients:

Formulation #1

| Ingredients | mg per capsule (% w/w) |
|---|---|
| Phenytoin Sodium | 100.0 mg (42.6%) |
| Lactose monohydrate | 57.00 mg (24.2%) |
| Talc | 11.75 mg (5%) |
| Confectioner's Sugar | 33.35 mg (14.9%) |
| Magnesium Stearate | 32.90 mg (14%) |
| Total weight | 235 mg (100%) |

Dissolution Results:

TABLE 2

Method: 900 mL purified water USP, USP apparatus 1, 50 rpm

| Time | Formulation #1 (% dissolved) | Dilantin® (% dissolved) |
|---|---|---|
| 15 min | 15 (10–20) | 13 (9–19) |
| 30 min | 34 (30–41) | 31 (24–37) |
| 60 min | 57 (52–61) | 58 (51–66) |
| 90 min | 72 (68–81) | 72 (67–81) |
| 120 min | 78 (76–80) | 83 (76–88) |

The dissolution results indicate in vitro equivalence of the extended-release formulation #1 to that of the brand product (i.e., Dilantin®).

Example 3

Effect of Mixing Time

Phenytoin sodium was mixed with lactose, talc and compressible sugar for 25 minutes. A high level of magnesium stearate was added and the powders were mixed further for 180 minutes. Samples were pulled out at 30, 60, 120 and 180 minutes and filled into capsules. The capsules dissolution results are presented in table 3 below:

TABLE 3

Dissolution Results
Method: 900 mL purified water USP, USP apparatus 1, 50 rpm

| Mixing time with magnesium stearate Time (min) | 30 min. % diss. | 30 min. % RSD* | 60 min. % diss. | 60 min. % RSD | 120 min. % diss. | 120 min. % RSD | 180 min. % diss. | 180 min. % RSD |
|---|---|---|---|---|---|---|---|---|
| 15 | 10 | 113.8 | 7 | 47.4 | 10 | 22.8 | 8 | 11.4 |
| 30 | 60 | 43.5 | 20 | 19.0 | 27 | 56.6 | 32 | 23.5 |
| 60 | 73 | 22.7 | 53 | 19.2 | 57 | 24.3 | 64 | 7.7 |
| 90 | 82 | 12.6 | 73 | 8.7 | 77 | 13.8 | 79 | 5.5 |
| 120 | 86 | 8 | 80 | 5.4 | 85 | 9.2 | 85 | 4.5 |

*RSD—relative standard deviation

Accordingly, these data indicate that the time of mixing is critical in affecting in vitro dissolution rate when phenytoin sodium capsules contain a high level of magnesium stearate. More than 30 minutes mixing of phenytoin and magnesium stearate is required.

Example 4

The Effect of Varying Magnesium Stearate Levels on Dissolution

Capsules containing phenytoin sodium were prepared according to the following: Formulations #2, #3, #4 and #5 with different magnesium stearate levels (i.e., 4.5, 7, 13 and 17% wt respectively), keeping lactose/confectionery sugar constant and applying the same multiple stages mixing sequences as in example 2: 3 hours mixing of phenytoin sodium and magnesium stearate, 30 minutes mixing with talc and 20 minutes mixing with lactose and compressible sugar.

TABLE 4

Dissolution Results
Method: 900 mL purified water USP, USP apparatus 1, 50 rpm

| Ingredients | Formulation #2 Mg/cap | Formulation #3 Mg/cap | Formulation #4 Mg/cap | Formulation #5 Mg/cap |
|---|---|---|---|---|
| Phenytoin Sodium | 100 | 100 | 100 | 100 |
| Talc | 12 | 12 | 12 | 12 |

TABLE 4-continued

Dissolution Results
Method: 900 mL purified water USP, USP apparatus 1, 50 rpm

| Ingredients | Formulation # 2 Mg/cap | Formulation # 3 Mg/cap | Formulation # 4 Mg/cap | Formulation # 5 Mg/cap |
|---|---|---|---|---|
| Lactose DC-21 | 71 | 67.5 | 58.5 | 52.5 |
| Confectionery sugar | 41.4 | 39 | 34 | 30.5 |
| Magnesium Stearate | 10.6 (4.5%) | 16.5 (7%) | 30.5 (13%) | 40.0 (17% wt) |
| Total weight | 235 mg | 235 mg | 235 mg | 235 mg |

The following table 5 summarizes the effects of magnesium stearate levels on dissolution rate.

TABLE 5

Method: 900 mL purified water USP, USP apparatus 1, 50 rpm

| Time (min) | Formulation # 2 (% diss) | Formulation # 3 (% diss) | Formulation # 4 (% diss) | Formulation # 5 (% diss) |
|---|---|---|---|---|
| 15 | — | 89 | 17 | 13 |
| 30 | 93 | 89 | 35 | 27 |
| 60 | 95 | 96 | 55 | 49 |
| 90 | — | 95 | 68 | 63 |
| 120 | 96 | 95 | 76 | 71 |

Accordingly, the present data indicate that there is a correlation between the level of magnesium stearate and the dissolution rate. While 4.5% wt and 7% wt magnesium stearate exhibited a dissolution rate similar to that of prompt formulation of phenytoin sodium, when the levels of magnesium stearate were increased to 13% wt and 17% wt, the dissolution rates for phenytoin sodium capsule were reduced. The dissolution rates were similar to that of Dilantin®.

Example 5

The Effect of Blender Types

Capsules containing phenytoin sodium were prepared according to the following: Formulation #6 was prepared with magnesium stearate (14% wt) and blended using different blender types. V-blender and Key high shear mixer were used. All excipients, except for magnesium stearate, were mixed for 25 minutes. The optimal mixing time with magnesium stearate in each experiment was determined by testing the dissolution rate at different blending time points. A comparison between the optimal results for the two blender types: V-blender—180 minutes mixing with magnesium stearate, Key high shear mixer—10 minutes mixing with magnesium stearate), indicated the preference of the V-blender based on the variability in dissolution results. (see tables 6 and 7).

TABLE 6

| Ingredients | Formulation # 6 mg/cap |
|---|---|
| Phenytoin Sodium | 100 |
| Talc | 11.75 |
| Lactose DC-21 | 57 |
| Compressible sugar | 33.35 |
| Magnesium Stearate | 32.9 |
| Total weight | 235 mg |

The following Table 7 summarizes the effect of different blender types on dissolution rate.

TABLE 7

Method: 900 mL purified water USP, USP apparatus 1, 50 rpm

| Time (min) | V-Blender (180 min) | | Key Blender (10 min) | | Dilantin ® | |
|---|---|---|---|---|---|---|
|  | % diss. | % RSD | % diss. | % RSD | % diss. | % RSD |
| 15 | 8 | 11.4 | 5 | 65.4 | 11 | 17.3 |
| 30 | 32 | 23.5 | 31 | 66.5 | 30 | 11.8 |
| 60 | 64 | 7.7 | 58 | 24.4 | 60 | 4.5 |
| 90 | 79 | 5.5 | 73 | 11.4 | 75 | 2.7 |
| 120 | 85 | 4.5 | 80 | 7.6 | 82 | 1.7 |

These data indicate that when a comparatively high percentage of magnesium stearate was used, the dissolution rate for phenytoin sodium capsule matched that of the brand product, Dilantin, irrespective of the blender type used.

Example 5

A) Effect of Storage Under Accelerated Conditions on Dissolution Rate.

As further controls, an additional capsule formulation containing phenytoin sodium and magnesium stearate was prepared (formulation #7). The ingredients are listed in Table 8. Accelerated conditions represent storage at 40° C. at 75% relative humidity for 3 months.

TABLE 8

| Ingredients | Formulation # 7 mg/cap |
|---|---|
| Phenytoin Sodium | 100 |
| Talc | 12 |
| Pharmatose DCL-15 (Lactose) | 58.5 |
| Confectionary Sugar | 34 |
| Magnesium Stearate | 30.5 (13% wt) |
| Total weight | 235 mg |

The following Table 9 summarizes the effect of storage of phenytoin sodium (formulation #7) under accelerated conditions on dissolution rate.

TABLE 9

| Method: 900 mL purified water USP, USP apparatus 1, 50 rpm | | | |
|---|---|---|---|
| Time (min) | % diss. ($T_0$) | % diss. (1 month) | % diss. (2 month) |
| 15 | 17 | 9 | 8 |
| 30 | 35 | 26 | 22 |
| 60 | 55 | 47 | 43 |
| 90 | 68 | 57 | 56 |
| 120 | 76 | 64 | 65 |

$T_0$: in vitro release was measured right after the capsules were prepared
1 month: in vitro release was measured after 1 month storage (40° C., 75% RH)
2 month: in vitro release was measured after 2 month storage time (40° C., 75% RH)

The present data confirm that reduction in dissolution rate is achievable with high levels of magnesium stearate.

Example 6

Effect of Addition of Hydroxypropylmethyl Cellulose (HPMC, Hypromellose)

A) Effects of Varying Concentrations and Different Types of HPMC (Methocels) on Dissolution Rate It was found that addition of HPMC to the pharmaceutical formulation of the present invention keeps the dissolution rate within the range of specifications throughout the product's shelf life.

The following studies relate to capsule formulations including phenytoin sodium, magnesium stearate and HPMC. Varying concentrations of HPMC as well as different grades of HPMC were used. The procedure of preparing these capsule formulations was the same; namely, all the excipients except magnesium stearate were mixed for 25 min, then magnesium stearate was added and the final blend was mixed for 5 more minutes.

The ingredients of such phenytoin sodium formulation having a high level of magnesium stearate and a low level of methocel are listed in Table 12.

TABLE 12

| | Phenytoin Sodium 100 mg Capsules | | | |
|---|---|---|---|---|
| Ingredients | Formulation # 9 mg/cap | Formulation # 10 mg/cap | Formulation # 11 mg/cap | Formulation # 12 mg/cap |
| Phenytoin Sodium | 100 | 100 | 100 | 100 |
| Talc | 12.0 | 23.75 | 23.75 | 23.75 |
| Pharmatose DCL-15 | 63.2 | 46.75 | 46.75 | 46.75 |
| Nu-Tab | 29.3 | 29.25 | 29.25 | 29.25 |
| HPMC (Methocel K4M) | 7.0 | 11.75 | 7.05 | 9.4 |
| HPMC (Methocel K100LV) | — | — | 4.7 | — |
| Magnesium Stearate | 23.5 | 23.5 | 23.5 | 23.5 |
| Total weight | 235 mg | 235 mg | 235 mg | 235 mg |

The following Table 13 summarizes the effect of the phenytoin sodium formulation containing magnesium stearate and HPMC on the dissolution rate.

TABLE 13

| | Method: 900 mL purified water USP, USP apparatus 1, 50 rpm | | | | | | | | |
|---|---|---|---|---|---|---|---|---|---|
| | Formulation # 9 | | Formulation # 10 | | Formulation # 11 | | Formulation # 12 | | Dilantin ® |
| Time (min.) | % diss | % RSD | % diss | % RSD | % diss | % RSD | % diss | % RSD | % diss | % RSD |
| 15 | 29 | 37.1 | 9 | 55.3 | 20 | 30.2 | 13 | 62.6 | 13 | 41.7 |
| 30 | 57 | 12.9 | 32 | 31.8 | 38 | 21.8 | 32 | 32.6 | 31 | 12.4 |
| 60 | 81 | 7.5 | 62 | 23.2 | 65 | 25.6 | 62 | 19.7 | 60 | 6.6 |
| 90 | 89 | 4.0 | 78 | 14.8 | 77 | 18.0 | 75 | 18.5 | 74 | 5.0 |
| 120 | 92 | 2.3 | 85 | 8.4 | 87 | 12.9 | 83 | 16.0 | 81 | 3.3 |

Example 7

Effect of Magnesium Stearate and/or HPMC (Methocel) Concentrations on Dissolution Rate We prepared additional capsule formulations containing phenytoin sodium, high levels of magnesium stearate and varying amounts of HPMC (methocel). The procedure in preparing these capsule formulations was the same; namely, all the excipients including magnesium stearate were mixed for 30 min. The specific ingredients of such phenytoin sodium formulations are listed in Table 14.

TABLE 14

| Ingredients | Formulation #13 mg/cap | Formulation #14 mg/cap | Formulation #15 mg/cap | Formulation #16 Mg/cap |
|---|---|---|---|---|
| Phenytoin Sodium | 100 | 100 | 100 | 100 |
| Pharmatose DCL-15 | 47 | 52 | 52 | 49 |
| Talc | 24 | 24 | 24 | 24 |
| Confectionery sugar | 29 | 29 | 29 | 29 |
| HPMC (Methocel K4M) | 9.5 (4%) | 9.5 (4%) | 12 (5%) | 12 (5%) |
| Magnesium Stearate | 23.5 (10%) | 18.5 (8%) | 16 (7%) | 19 (8%) |
| Total weight | 233 mg | 233 mg | 233 mg | 233 mg |

The following Table 15 summarizes the effect of the phenytoin sodium formulations containing high levels of magnesium stearate and varying amounts of HPMC (methocel) on dissolution rate

TABLE 15

USP Method: 900 mL purified water USP, USP apparatus 1, 75 rpm

| Time (min.) | Formulation #13 % diss | Formulation #13 % RSD | Formulation #14 % diss | Formulation #14 % RSD | Formulation #15 % diss | Formulation #15 % RSD | Formulation #16 % diss | Formulation #16 % RSD | Dilantin ® % diss | Dilantin ® % RSD | Dilantin ® % diss | Dilantin ® % RSD |
|---|---|---|---|---|---|---|---|---|---|---|---|---|
| 15 | 10 | 7.5 | 15 | 16.3 | 15 | 13.3 | 9 | 84 | — | — | — | — |
| 30 | 25 | 6.6 | 34 | 13.1 | 32 | 8.3 | 26 | 7.1 | 31 | 5.7 | 34 | 4.1 |
| 60 | 51 | 5.4 | 67 | 12.1 | 66 | 10.4 | 54 | 4.3 | 53 | 3.5 | 60 | 5.6 |
| 90 | 67 | 6.0 | 84 | 5 | 89 | 3.1 | 75 | 6.0 | 65 | 2.9 | 75 | 5.9 |
| 120 | 78 | 6.7 | 91 | 2.7 | 92 | 2.1 | 86 | 4.9 | 73 | 3.2 | 82 | 2.9 |

Example 8

Effect of Varying Concentrations of Talc on Dissolution Rate

We prepared two capsule formulations containing phenytoin sodium, magnesium stearate and a varying amount of talc. The formulations also contained a low level of HPMC (methocel). The specific ingredients of such phenytoin sodium formulations are listed in Table 16.

TABLE 16

| Ingredients | Formulation #17 mg/cap | Formulation #18 mg/cap |
|---|---|---|
| Phenytoin Sodium | 100 | 100 |
| Talc | 23.75 (10%) | 12 (5%) |
| Lactose DC-21 | 46.75 | 58.5 |
| Compressible Sugar | 29.25 | 29.25 |
| HPMC (Methocel K4M) | 11.75 | 11.75 |
| Magnesium Stearate | 23.5 | 23.5 |
| Total weight | 235 mg | 235 mg |

The following Table 17 summarizes the effects of the phenytoin sodium formulation containing a high level of magnesium stearate, a small amount of HPMC (methocel) and varying amount of Talc on dissolution rate.

TABLE 17

USP dissolution method: 900 ml purified water, USP apparatus 1, 50 rpm.

| Time (min.) | Formulation #17 % diss | Formulation #17 % RSD | Formulation #18 % diss | Formulation #18 % RSD | Dilantin ® % diss | Dilantin ® % RSD |
|---|---|---|---|---|---|---|
| 15 | 6 | 28.6 | 7 | 31 | 11 | 22.0 |
| 30 | 19 | 18.4 | 20 | 22.4 | 30 | 12.0 |
| 60 | 51 | 19.7 | 53 | 9.5 | 54 | 7.0 |
| 90 | 71 | 17.1 | 84 | 3.6 | 68 | 5.0 |
| 120 | 80 | 13.5 | 92 | 3.6 | 76 | 3.0 |

Accordingly, the present data indicate that the amount of Talc may affect dissolution rate when phenytoin sodium capsules contain a comparatively high percentage of magnesium stearate as well as a comparatively small amount of HPMC (methocel).

Example 9

Pharmacokinetic Profile

Bioavailability Study Under Fasting and Non-Fasting Conditions

The present study was conducted to compare the relative bioavailability (rate and extent of absorption) of pharmaceutical formulation of the present invention with that of the phenytoin extended-release capsules marketed under the trademark Dilantin® Kapseals® by Parke-Davis following a single oral dosage (1×100 mg) in healthy adult volunteers administered under fasting and non-fasting conditions. Table 18 provides the formulation used for the study.

TABLE 18

Formula for Phenytoin Sodium Capsules

| Ingredient | Mg/Capsule |
|---|---|
| Phenytoin Sodium | 100.0 |
| Lactose Monohydrate | 47.0 |
| Talc | 24.0 |
| Confectioner's Sugar | 31.5 |
| Hypromellose (Methocel K4M) | 9.5 |
| Magnesium Stearate | 21.0 |
| Total | 233.0 |

Bioavailability Study Under Fasting and Non-Fasting Conditions

The present study was conducted to compare the relative bioavailability (rate and extent of absorption) of present extended-release formulation of phenytoin sodium (containing a high level of magnesium stearate and a low level of hydroxoylmethyl cellulose) with that of Dilantin® Kapseals® by Parke-Davis following a single oral dosage (1×100 mg) in healthy adult volunteers administered under fasting and non-fasting conditions.

Evaluation of Study Participants: Subjects were selected from non-institutionalized volunteers consisting of university students and members of the community at large. All volunteers selected for this study were healthy men 18 years of age or older at the time of dosing. The weight range did not exceed ±20% for height and body frame as per desirable weights for adults—1983 Metropolitan Height and Weight Table. Each volunteer completed the screening process within 28 days prior to period I dosing. The screening clinical laboratory procedures included: general observation, physical examination, demographics, medical and medication history, an electrocardiogram, sitting blood pressure and heart rate, respiratory rate and temperature. Blood was withdrawn to evaluate hematology, clinical chemistry, HIV antibody, hepatitis B surface antigen, hepatitis C antibody. Urine was collected to evaluate urinalysis and urine drug screen.

Study Design:

Fasting Study: A single-dose, two-way crossover, fasting study was conducted. Two study periods were used. Approximately 10 hours prior to and until at least 24 hours after dosing each period. Forty-four (44) healthy adult male volunteers and no alternates were initiated for the study. At least 14 days were allowed to permit washout between doses. After dosing, subjects remained in an upright position for four hours. A sitting blood pressure and radial heart rate were measured prior to dosing and at 12 and 24 hours after each dose.

One capsule of the present extended-release formulation (100 mg) was randomly given to subjects with 240 mL of room temperature water after an overnight fast. One capsule of US reference product (i.e., 100 mg Dilantin® Kapseals®) by Parke-Davis was also randomly provided to subjects with 24 mL of room temperature water after an overnight fast. No fluid, except that given with drug administration, was allowed from 1 hour prior to dose administration until 2 hour after dosing. At 2 hours post-dose, subjects were allowed to consume 240 mL of water. Clear fluids, such as water, wereallowed during fasting. A light snack wasserved approximately 10 hours prior to dose administration after which a fast (except water) would be maintained until at least 4 hours after dosing. Subjects were randomized prior to given a capsule of either tested product or reference product.

Non-Fasting Study: A single-dose, two-wary crossover, non-fasting study was conducted. Two study periods were used. Approximately 10 hours prior to and until at least 24 hours after dosing each period. Thirty-six (36) healthy adult male volunteers and no alternates were initiated for the study. At least 14 days were allowed to permit washout between doses. After dosing, subjects remained in an upright position for four hours. A sitting blood pressure and radial heart rate were measured prior to dosing and at 12 and 24 hours after each dose.

One capsule of the present extended-release formulation (100 mg) was randomly given to subjects with 240 mL of room temperature water 30 minutes after initiation of a standardized, high fat breakfast preceded by an overnight fast. The standardized, high fat breakfast consisting of the following: (i) two eggs fried in butter; (ii) two strips of bacon; (iii) two slices of toast with butter; (iv) four ounces of hash brown; (v) eight fluid ounces (240 mL of whole milk); and, (vi) potatoes.

One capsule of US reference product (i.e., 100 mg Dilantin® Kapseals® by Parke-Davis was also randomly provided to subjects with 24 mL of room temperature water 30 minutes after initiation of a standardized, high fat breakfast preceded by an overnight fast. No fluid, except that given with drug administration, was allowed from 1 hour prior to dose administration until 2 hour after dosing. At 2 hours post-dose, subjects were allowed to consume 240 mL of water. A light snack was served approximately 10 hours prior to dose administration. Following consumption of the standardized breakfast, a fast (except water) would be maintained until at least 4 hours after dosing. Clear fluids, such as water, were allowed during fasting. Subjects were randomized prior to being given a capsule of either tested product or reference product.

Sampling Details: Blood sample (1×7 mL) was collected EDTA vacutainers. Blood samples within one hour prior to dosing (0 hour) and after dosing administration at 1, 2, 3, 4, 5, 6, 7, 8, 9, 10, 11, 12, 16, 24, 48, 72 and 96 hours). 18 blood samples per period×2 study periods (i.e., total of 36 samples, 252 mL total volume) were collected. Blood samples were collected by direct venipuncture, centrifuged at approximately 2,400 rpm and 4° C. for 15 minutes, the plasma was pipetted into amber polypropylene tubes, frozen, and stored at approximately −20° C. or colder until analysis.

Bioanalytical Analysis, and Statistical Analysis: Plasma concentrations of phenytoin was measured using a validated bioanalytical method. The statistical analysis was conducted using appropriate pharmacokinetic parameters and statistical analysis of the data.

Pharmacokinetics & Statistical Analysis:

Plasma phenytoin concentrations were determined and the pharmacokinetic parameters were calculated using WinNonlin™, Version 4.1, software designed specifically for analyzing pharmacokinetic data. WinNonlin™ Model 200 for extravascular input was utilized. All other computations were completed using SAS®, Version 8.2 for Windows. Microsoft® Excel® 97 and SAS®, Version 8.2 for Windows, were used to produce the tables and graphs.

The following pharmacokinetic parameters were computed from the plasma concentration data using the actual sample collection times:

$AUC_{o-t}$—Area under the plasma concentration-time curve (ng~hr/mL) from time zero to the time of the last quantifiable concentration (t), calculated using the linear trapezoidal rule: $\Sigma i(t_i-t_i\cdot 1)(C_i+C_i\cdot 1)/2$, i=1 to t, where $C_i$ is the plasma concentration at time $t_i$.

$AUC_{0-\infty}$—Area under the plasma concentration curve from time zero extrapolated to infinity (ng-hr/mL), calculated by $AUC0-t+(C_{last}/ke)$, where $C_{last}$ is the last quantifiable concentration and ke is the terminal elimination rate constant.

$C_{max}$—Maximum or peak concentration, obtained by inspection (ng/mL).

$T_{max}$—Time of maximum or peak concentration, obtained by inspection (hr).

Ke—Terminal elimination rate constant (1/hr). This value was estimated by linear regression on the terminal phase of the semi-logarithmic concentration versus time curve.

$T_{1/2}$—Half life of the product (hr), calculated by ln(2)/ke (Natural logarithmic (ln) transformations were computed for $AUC_{0-T}$, $AUC_{0-\infty}$ and $C_{max}$)

Statistical Analysis

An analysis of variance (ANOVA) was performed on each of the pharmacokinetic parameters using SAS® software. The ANOVA model containing factors for sequence of products, subjects within sequence, periods and products was utilized in comparing the effects between the test and reference products. Differences were declared statistically significant at the 5% level.

Since the subjects were dosed in two groups, an analysis of variance (ANOVA) was used to detect the presence of a group-by-product interaction. The ANOVA model containing factors for group, sequence, group-by-sequence, subject within group-by-sequence, period within group, product, and group-by-product was utilized to detect the presence of a group-by-product interaction. If the group-by-product term was not significant (p-value>0.1), the term was removed from the model. This reduced model was then used to compare the effects between the test and reference products. Differences were declared statistically significant at the 5% level.

A 90% confidence interval about the ratio of the mean test value to mean reference value was calculated for all of the pharmacokinetic parameters. The power of the ANOVA to detect a difference equal to 20% of the reference mean was also calculated with the SAS® software. The calculations for the power and confidence interval used the least squares means (LSMEANS) and the standard error of the estimate, both generated by the SAS® software. The ratio of the geometric means for the ln-transformed data and the corresponding 90% confidence intervals were calculated for $AUC_{0-t}$, $AUC_{0-\alpha}$, and $C_{max}$, as well.

The lower limit of quantitation for phenytoin was 50 ng/mL. For statistical analysis, subject sample values below the lower limit of quantitation (BLQ) were reported as zero.

The statistical analysis was done using SAS®, Version 8.2 for Windows.

To establish bioequivalence under fasting conditions, the 90% confidence interval for the ratio of the geometric means between the product were to fall within the interval 80-125% for log-transformed $AUC_{0-t}$, $AUC_{0-\alpha}$, and $C_{max}$.

Table 19 summarizes the results of the analyses performed on the pharmacokinetic parameters.

TABLE 19

Summary of Ln Transformed Pharmacokinetic Parameters (a)

| Phenytoin | Ln-Transformed $C_{max..}$ | Ln-Transformed $AUC_{0-t}$ | Ln-Transformed $AUC_{0-\alpha}$ |
|---|---|---|---|
| Test Product of the present invention Geometric Mean | 1160.31 | 29961.63 | 3692.43 |
| Reference Product Geometric Mean | 1225.07 | 32505.03 | 35310.18 |
| % Ratio | 94.71 | 92.18 | 95.42 |
| 90% Confidence Interval | (89.14, 100.64) | (87.45, 97.15) | (92.16, 98.79) |

(b)

| Phenytoin | $C_{max..}$ | $AUC_{0-t}$ | $AUC_{0-\alpha}$ |
|---|---|---|---|
| Test Product of the present invention Least Squares Mean | 1190.16 | 32158.32 | 36110.54 |
| Reference Least Squares Mean | 1266.49 | 35124.24 | 37998.76 |
| % Ratio | 93.97 | 91.56 | 95.03 |
| 90% Confidence Interval | (88.28, 99.66) | (86.97, 96.14) | (92.18, 97.88) |

(c)

| Phenytoin | $T_{max..}$ | $K_e$ | $t_{1/2}$ |
|---|---|---|---|
| Test Product of the present invention Least Squares Mean | 4.16 | 0.0444 | 17.11 |
| Reference Least Squares Mean | 4.88 | 0.0450 | 16.70 |
| % Ratio | 85.33 | 98.71 | 102.50 |
| 90% Confidence Interval | (63.16, 107.49) | (94.08, 103.33) | (96.79, 108.22) |

FIG. 1 shows the mean plasma concentration over time of the pharmaceutical formulation of the present invention as compared with the reference standard product.

What is claimed is:

1. A pharmaceutical formulation of phenytoin sodium comprising a dry blended powder in a capsule having from about 10% (w/w) to about 90% (w/w) phenytoin sodium, from 6% (w/w) to 20% (w/w) magnesium stearate and from about 1% (w/w) to about 7% (w/w) of a hydrophilic polymer, and wherein the in vitro dissolution profile for phenytoin sodium when tested using USP apparatus I in water at 75 rpm is:

(i) from about 20% (w/w) to about 40% (w/w) released in 30 minutes;
(ii) from about 40% (w/w) to about 85% (w/w) released in 60 minutes; and
(iii) not less than 70 percent (w/w) released in 120 minutes.

2. The pharmaceutical formulation of claim 1 wherein the hydrophilic polymer is selected from the group consisting of hydroxypropylmethyl cellulose, hydroxypropyl starch, hydroxypropyl cellulose, hydroxyethyl cellulose, carboxymethyl cellulose, polyethylene oxide, acacia, guar gum, tragacanth gum, xanthan and mixtures thereof.

3. The pharmaceutical formulation of claim 1, wherein the hydrophilic polymer is hydroxypropylmethyl cellulose.

4. The pharmaceutical formulation of claim 1 comprising from about 40% (w/w) to about 45% (w/w) phenytoin sodium, from 6% (w/w) to 10% (w/w) magnesium stearate, and from about 1% (w/w) to about 5% (w/w) hydroxypropylmethyl cellulose.

5. The pharmaceutical formulation of claim 1 comprising about 43% phenytoin sodium, about 9% (w/w) magnesium stearate and about 4% hydroxypropylmethyl cellulose.

6. The pharmaceutical formulation of claim 1 further comprising from about 5% (w/w) to about 15% (w/w) talc.

7. The pharmaceutical formulation of claim 1 further comprising from about 15% (w/w) to about 25% (w/w) lactose monohydrate.

8. A pharmaceutical formulation of phenytoin sodium comprising a dry blended powder in a capsule having about 43% (w/w) phenytoin sodium, about 9% (w/w) magnesium stearate, about 4% (w/w) hydroxypropyl methylcellulose, about 20% (w/w) lactose monohydrate, about 13% (w/w) confectioner's sugar and about 10% (w/w) talc.

9. The pharmaceutical formulation of claim 1 wherein the pharmaceutical formulation provides a peak plasma level of phenytoin from 4.5 hours to 11 hours after oral administration in a human.

10. The pharmaceutical formulation of claim 1 further comprising binders, glidants, lubricants, diluents, disintegrants and mixtures thereof.

11. A pharmaceutical formulation of phenytoin sodium comprising from about 10% (w/w) to about 90% (w/w) phenytoin sodium, from 6% (w/w) to 20% (w/w) magnesium stearate and from about 1% (w/w) to about 7% (w/w) of a hydrophilic polymer, wherein the formulation is produced by a dry-mix process and wherein the in vitro dissolution profile for phenytoin sodium when testing using USP apparatus I in water at 75 rpm is:
  (i) from about 20% (w/w) to about 40% (w/w) released in 30 minutes;
  (ii) from about 40% (w/w) to about 85% (w/w) released in 60 minutes; and
  (iii) not less than 70 percent (w/w) released in 120 minutes.

12. The formulation of claim 11, wherein the dry-mix process comprises the steps of:
  (a) screening a mixture of phenytoin sodium and a hydrophilic polymer through a 30 mesh sieve;
  (b) screening magnesium stearate through a 60 mesh screen;
  (c) mixing the phenytoin sodium, hydrophilic polymer from step (a) and magnesium stearate from step (b) together to form a dry blended powder comprising from 6% to 20% (w/w) magnesium stearate.

13. The pharmaceutical formulation of claim 12, wherein the process comprises filling a capsule with the dry blended powder from step (c).

14. The pharmaceutical formulation of claim 1, wherein the hydrophilic polymer is hydroxypropyl cellulose.

* * * * *